United States Patent
Quay et al.

(10) Patent No.: US 9,052,318 B2
(45) Date of Patent: Jun. 9, 2015

(54) ABSORBENT PAPER AND USE THEREOF FOR BREAST CANCER DETECTION

(71) Applicant: Atossa Genetics, Inc., Seattle, WA (US)

(72) Inventors: Steven C. Quay, Seattle, WA (US); Shu-Chih Chen, Seattle, WA (US)

(73) Assignee: ATOSSA GENETICS, INC., Seattle, WA (US)

(*) Notice: Subject to any disclaimer, the term of this patent is extended or adjusted under 35 U.S.C. 154(b) by 0 days.

(21) Appl. No.: 14/352,461

(22) PCT Filed: Oct. 24, 2012

(86) PCT No.: PCT/US2012/061733
§ 371 (c)(1),
(2) Date: Apr. 17, 2014

(87) PCT Pub. No.: WO2013/063147
PCT Pub. Date: May 2, 2013

(65) Prior Publication Data
US 2014/0287430 A1    Sep. 25, 2014

Related U.S. Application Data

(60) Provisional application No. 61/550,855, filed on Oct. 24, 2011.

(51) Int. Cl.
| | | |
|---|---|---|
| *G01N 31/00* | (2006.01) |
| *G01N 33/53* | (2006.01) |
| *G01N 33/574* | (2006.01) |
| *G01N 33/68* | (2006.01) |
| *A61B 10/00* | (2006.01) |
| *C12Q 1/06* | (2006.01) |

(52) U.S. Cl.
CPC ...... *G01N 33/57415* (2013.01); *G01N 33/6836* (2013.01); *A61B 10/0041* (2013.01); *C12Q 1/06* (2013.01); *G01N 33/683* (2013.01); *A61B 10/0045* (2013.01)

(58) Field of Classification Search
CPC . A61M 1/06; G01N 33/57415; G01N 33/683; A61B 10/0041; A61B 10/0045; C12Q 1/06
See application file for complete search history.

(56) References Cited

U.S. PATENT DOCUMENTS

| | | | |
|---|---|---|---|
| 4,920,059 A | 4/1990 | Moeremans et al. | |
| 5,798,266 A | 8/1998 | Quay et al. | |
| 6,287,521 B1 | 9/2001 | Quay et al. | |
| 6,328,709 B1 | 12/2001 | Hung et al. | |
| 6,629,936 B2 | 10/2003 | Hung et al. | |
| 6,676,610 B2 | 1/2004 | Morton et al. | |
| 6,689,073 B2* | 2/2004 | Quay | 600/573 |
| 6,887,210 B2* | 5/2005 | Quay | 600/573 |
| 7,128,877 B2* | 10/2006 | Quay et al. | 600/573 |
| 7,128,887 B2 | 10/2006 | Huhn | |
| 2002/0013539 A1 | 1/2002 | Hung et al. | |
| 2003/0211624 A1 | 11/2003 | Goldknopf et al. | |
| 2006/0030787 A1 | 2/2006 | Quay | |
| 2006/0178601 A1 | 8/2006 | Wang et al. | |
| 2010/0221742 A1 | 9/2010 | Suri | |
| 2010/0256464 A1 | 10/2010 | Love et al. | |
| 2013/0115629 A1 | 5/2013 | Quay et al. | |
| 2013/0130310 A1 | 5/2013 | Quay et al. | |

FOREIGN PATENT DOCUMENTS

| | | |
|---|---|---|
| EP | 606187 | 1/1993 |
| JP | 09-149890 | 6/1997 |
| WO | WO2013/063147 | 5/2013 |
| WO | WO2013/063150 | 5/2013 |

OTHER PUBLICATIONS

Advantec MFS, Inc., Mixed cellulose esters (MCE) membrane filters, 2001-2006, at http://www.advantecmfs.com/filtration/membranes/mb_nitroMCE.shtml. Access date Apr. 8, 2014.
BioTrace™ NT Nitrocellulose Transfer Membrane, Pall Corporation, http://www.pall.com/main/laboratory/product.page?id=20011—access date Apr. 7, 2014.
Ceriani et al. Proc. Natl. Acad. Sci. USA 74:582-586, 1982.
Ceriani et al., Breast Cancer Res. Treat. 15:161-174, 1990.
Danscher et al., Colloidal Gold Amplification, the Journal of Histochemistry and Cytochemistry, 31: No. 12, 1394-1398 (1983).
De Mey, Colloidal Gold Methods, Immunocytochemistry, Chapt. 6, pp. 82-112 (1983).
King et al, Cancer, 2002, 96:244-249.

(Continued)

*Primary Examiner* — Lisa Cook
(74) *Attorney, Agent, or Firm* — Wilson Sonsini Goodrich & Rosati

(57) ABSTRACT

Biological samples of mammary fluid or components thereof are obtained using a breast pump device coupled with an absorbent paper or membrane, optionally facilitated by administering oxytocin to the subject. The breast pump device stimulates expression of mammary fluid and provides for collection of diagnostic samples on the absorbent paper or membrane to evaluate breast disease, including cancer. The biological sample may include fluid containing one or more of cells or cellular components, proteins, glycoproteins, peptides, nucleotides or other desired constituents comprising a breast disease marker. Absorbent paper or membrane, and methods relating to the paper or membrane, and a breast pump device are also provided.

14 Claims, 1 Drawing Sheet

(56) References Cited

OTHER PUBLICATIONS

Laakso, M., et al. "Cytokeratin 5/14-positive breast cancer: true basal phenotype confined to BRCA1 tumors." Modern Pathology, vol. 18, No. 10, 2005, p. 1321-1328.

Marc Moeremans, et al., "Sensitive Colloidal Metal (Gold or Silver) Staining of Protein Blots on Nitrocellulose Membranes" in Analytical Biochemistry 145, 315-321 (1985).

Nagle et al, J Histochem. Cytochem., 1986; 34:869-881.

PCT Application PCT/US2012/061738 International Search Report and Written Opinion dated Feb. 1, 2013.

PCT/US2012/061733 International Search Report and Written Opinion dated Mar. 4, 2013.

Reisenbichler, E., et al. "Luminal cytokeratin expression profiles of breast papillomas and papillary carcinomas and the utility of a cytokeratin 5/p63/cytokeratin 8/18 antibody cocktail in their distinction." Modern Pathology, vol. 24, No. 2, 2011, p. 185-193.

Rosner et al., Cancer Invest. 13:573-582, 1995.

Tacha, D., et al. "A Rapid Double Immunostaining Technique with a Single Cocktail of CK5, CK14, p63, CK7 and CK18 Distinguishes Between Hyperplasia of the Usual Type, Atypical Hyperplasia, Microinvasive and Basal Phenotype Breast Cancers." Biocare Medical (www.biocare.net), Mar. 2, 2009, p. 1-4.

Al-Maghraby et al. The Diagnostic Utility of CK5/6 and p63 in Fine-Needle Aspiration of the Breast Lesions Diagnosed as Proliferative Fibrocystic Lesion. Diagnostic Cytopathology 40(2):141-147 (2010).

Cai et al. Applications of gold nanoparticles in cancer nanotechnology. Nanotechnology Science and Applications 1:17-32 (2008).

Clubbs et al. Basal Cell Induced Differentiation of Noncancerous Prostate Epithelial Cells (RWPE-1) by Glycitein. Nutrition and Cancer 61(3):390-396 (2009).

Imayama et al. Presence of Elevated Carcinoembryonic Antigen on Absorbent Disks Applied to Nipple Area of Breast Carcinoma Patients. Cancer 78:1229-1234 (1996).

King et al. Cellular Composition of the Nipple Aspirate Specimen of Breast Fluid. American Journal of Clinical Pathology, American Society for clinical Pathology 64(6):728-745 (1975).

Krishnamurthy et al. Nipple aspirate fluid cytology in breast carcinoma. Cancer 99(2):97-104 (2003).

Mannello et al. Increased shedding of soluble fragments of P-cadherin in nipple aspirate fluids from women with breast cancer. Cancer Sci. 99:2160-2169 (2008).

Qin et al. Nipple aspirate fluid expression of urokinase-type plasminogen activator, plasminogen activator inhibitor-1, and urokinase-type plasminogen activator receptor predicts breast cancer diagnosis and advanced disease. Ann Surg Oncol. 10(8):948-953 (2003).

Sauter et al. Nipple aspirate fluid: a promising non-invasive method to identify cellular markers of breast cancer risk. British Journal of Cancer 76(4):494-501 (1997).

Sauter et al. Prostate-specific antigen expression in nipple aspirate fluid is associated with advanced breast cancer. Cancer Detection and Prevention 28(1):27-31, 2004.

U.S. Appl. No. 13/659,832 Office Action dated Nov. 17, 2014, LVC Mar. 31, 2015.

Yazid et al. Synthesis and characterization of gold nanoparticles supported on zinc oxide via the deposition-precipitation method. Turk. J. Chem. 34:639-650 (2010).

* cited by examiner

A.
B.
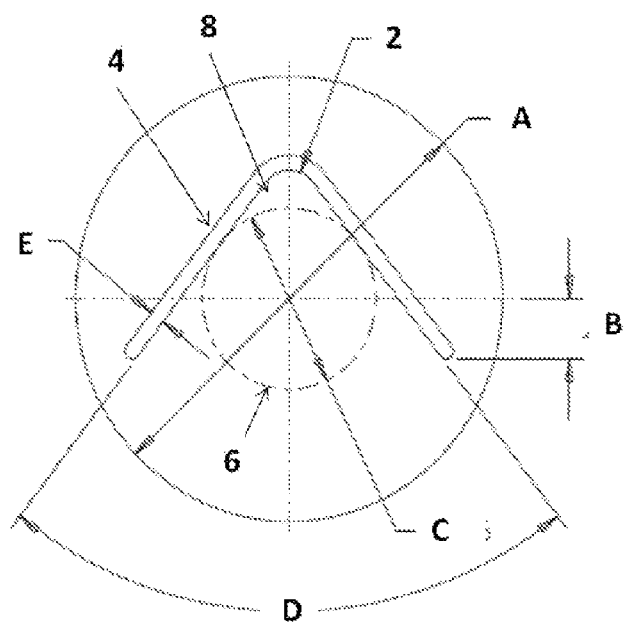
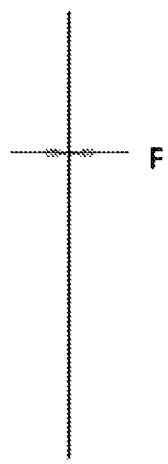

ABSORBENT PAPER AND USE THEREOF FOR BREAST CANCER DETECTION

CROSS-REFERENCE

This application is the National Phase entry of International Application No. PCT/US2012/061733, filed Oct. 24, 2012, which claims the benefit of U.S. Provisional Application No. 61/550,855, filed Oct. 24, 2011, both of which are incorporated herein by reference in their entireties.

BACKGROUND OF THE INVENTION

Breast cancer is by far the most common form of cancer in women, and it is the second leading cause of cancer death in humans. Despite advances in diagnosing and treating breast cancer, the prevalence of this disease has been steadily rising at a rate of about 1% per year since 1940. Today, the likelihood that a women living in North America will develop breast cancer during her lifetime is one in eight.

The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited.

SUMMARY OF THE INVENTION

The clinical utility of nipple aspirate fluid for helping in breast health management has been hampered over the last 50 years by the current clinical methodology of collecting and measuring the presence of fluid. In fact, using current technology, up to 50% of all women are non-secretors, that is, they are judged to not produce nipple aspirate fluid (NAF); this, in turn, means that these women cannot be tested for diagnosis of early stage breast cancer using non-invasive procedures using current technology.

Additionally, paper used to collect fluid from non-secreting and secreting women using current technology results in a significant number of paper cuts to the nipple tissue, rendering sample collection painful for women undergoing testing.

The present inventor identified for the first time a new absorbent paper or membrane that significantly reduces the number of paper cuts during sample collection. The present inventor also identified for the first time herein, that the new absorbent paper or membrane allows very low sample volume collection from women who were previously considered non-secretors. Even in view of the low sample volume, the present inventor identified for the first time that the samples from women considered non-secretors could be successfully assessed for protein and number of cells for early stage breast cancer risk assessment. Prior to the present invention, samples from women considered non-secretors were thrown away and the women had to be tested using invasive procedures. The embodiments presented herein, therefore, represent a significant advance in the field of early stage breast cancer risk assessment for a patient population which, previously, could not be assessed using non-invasive procedures. The present methods also allow for early stage breast cancer risk assessment of women who are classically secretors. The present methods allow for greater sensitivity of protein detection in a sample, thereby increasing the ability of practitioners to detect breast cancer at an earlier stage of disease progression. The present methods can detect protein in nipple aspirate fluid (NAF) at a concentration of as low as about 70 picograms (pg). This represents a significant advance over prior techniques which detected protein in NAF samples of secretors at a concentration of about 350 nanograms (ng).

Provided herein is a method of identifying women at low risk of future breast cancer, comprising obtaining a sample of nipple aspirate fluid; testing for protein in said sample; and testing for cells in said sample, wherein the lowest risk is associated with a sample that contains protein and is acellular.

Also provided herein is a method of identifying risk of a patient for breast cancer or diagnosing a patient at low risk of breast cancer, comprising: comparing, using a general purpose computer, the concentration of protein in a nipple aspirate fluid sample and the number of cells in said sample, to the concentration of protein and number of cells in a population of patients known to have breast cancer and/or to a population of patients known not to have breast cancer; wherein the lowest risk is associated with a sample that contains protein and is acellular or contains one cell.

The patient population identified as being at lowest risk for breast cancer is associated with a sample that contains protein and is acellular or contains one cell. In one embodiment, the sample contains no cells (i.e., is acellular). In another embodiment, low risk is associated with a sample that contains protein and contains one cell. The risk of breast cancer increases with increasing number of cells.

Patients to be diagnosed with a method provided herein include those classically designated as non-secretors and secretors of nipple aspirate fluid (NAF).

In one embodiment, the patient is classically designated as a non-secretor of nipple aspirate fluid.

Nipple aspirate fluid sample is collected on absorbent paper or a membrane. Absorbent paper or a membrane that may be used in the present methods includes paper or a membrane of the size and dimensions as illustrated in FIG. 1. The paper or membrane may be made of, for example, microcellulose, mixed cellulose ester paper or nitrocellulose. This new design results in significantly fewer cuts to nipple tissue during sample collection compared to paper that is currently marketed for NAF collection.

The absorbent paper or membrane is washed and the effluent is collected and assessed for number of cells. In one embodiment, cytology of cells, if any, in said sample is analyzed using any conventional method including, but not limited to, microscopy, flow cytometry, immunohistochemistry, or a combination thereof. A clinician can determine if cells, if present in the sample, are normal contain one or more characteristics of cancer cells. In one non-limiting example, cell samples may be stained with hemolysin and eosin.

Protein measured by the methods described herein is total protein content of the sample. The paper is then exposed to colloidal gold or colloidal silver and the total protein content (concentration) is determined.

In one aspect, if a sample contains from about 50 pg to about 0.5 ng of protein, and does not contain cells, a patient is identified as being at low risk for breast cancer.

Alternatively, if the sample contains at least about 300 ng of protein and two (2) or more cells, a patient is identified for further evaluation of breast cancer or diagnosed as at medium or high risk for breast cancer. In one embodiment, the concentration of protein in a sample is from about 300 ng of protein to about 2 μg of protein and a patient is diagnosed at being at higher risk for breast cancer and, in some cases, is identified for further assessment. The cell fraction of the sample, in such a case, may contain about 2 cells to about 50 cells. Such a cell fraction may, in another case, may contain at least ten (10) cells.

Provided herein is an absorbent paper or membrane having the characteristics and dimensions as illustrated in FIG. 1, where the absorbent paper or membrane is made using microcellulose, mixed cellulose ester paper or nitrocellulose. In one embodiment, the absorbent paper or membrane comprises mixed cellulose ester.

A method of detecting protein in a sample of nipple aspirate fluid (NAF) comprising collecting the NAF on an absorbent paper or membrane and detecting the protein with a colloidal metal particle suspension, wherein the method can detect protein at a concentration of between 0.5 ng and 500 ng per sample. In one embodiment, the metal particle suspension comprises colloidal gold.

A significant advance of the present absorbent paper or membrane is that is does not cut tissue to the extent that current filter paper does; thus, a patient undergoing assessment is subject to less pain and discomfort during the collection procedure. In one embodiment, tissue exposed to the paper or membrane is nipple tissue.

Provided herein is the use of the absorbent paper or membrane as described herein in a method of identifying a patient at low risk of breast cancer or diagnosing a patient at low risk of breast cancer. In one aspect, the absorbent paper or membrane is used in any of the methods described herein or in any other method of nipple aspirate fluid collection for any use.

Provided herein is method of identifying risk of a patient for breast cancer or diagnosing a patient at low risk of breast cancer, comprising: collecting nipple aspirate fluid on absorbent paper or membrane; washing said absorbent paper or membrane with buffered solution to collect cells, if any; counting the number of cells in said sample and, optionally, determining the cytology of said cells, if any; staining said absorbent paper or membrane with colloidal gold or colloidal silver and determining the concentration of protein on said filter paper; and comparing, the concentration of protein in said nipple aspirate fluid and the number of cells in said fluid, to the concentration of protein and number of cells in a population of patients known to have breast cancer and/or to a population of patients known not to have breast cancer; wherein the lowest risk is associated with a sample that contains protein and is acellular or contains one cell.

Provided herein is a method of diagnosing risk of a patient for breast cancer, comprising: collecting nipple aspirate fluid on absorbent paper or membrane, wherein said NAF sample is obtained from classical providers and non-providers; washing said absorbent paper with buffered solution to collect cells, if any; counting the number of cells in said sample and, optionally, determining the cytology of said cells, if any; staining said absorbent paper or membrane with colloidal gold or colloidal silver and determining the concentration of protein on said filter paper; and comparing, the concentration of protein in said nipple aspirate fluid and the number of cells in said fluid, to the concentration of protein and number of cells in a population of patients known to have breast cancer and/or to a population of patients known not to have breast cancer; wherein the lowest risk is associated with a sample that contains protein and is acellular or contains one cell.

Also provided herein is a method of identifying risk of developing breast cancer in an individual in need thereof, comprising: detecting the total amount of protein and/or number of cells in a nipple aspirate fluid sample absorbed onto an absorbent paper as illustrated in FIG. 1, wherein said absorbent paper comprises microcellulose, mixed cellulose ester paper or nitrocellulose; and identifying the risk for developing breast cancer based on the total amount of protein and/or the number of cells of the nipple aspirate fluid sample.

In one embodiment, the sample is acellular and the patient is identified as at the lowest risk for breast cancer. In another embodiment, the sample contains one cell and the patient is identified as at low risk for breast cancer. In yet another embodiment, the sample contains more than 2 cells and the patient is identified for further assessment.

In one embodiment, the total protein concentration of each breast is determined and, if the total protein concentration of one sample is greater than 300 ng, the patient is identified for further assessment of breast cancer. Alternatively, the total protein concentration of each breast is determined and, if the total protein concentration of each sample is at, or below 200 ng protein, the patient is identified as being at low risk for breast cancer.

In one embodiment, the nipple aspirate fluid is collected on absorbent paper or membrane following massaging of breast tissue and suction with a mammary aspirate specimen cytology test (MASCT™) device as described in Example 1. As used herein, a "MASCT™ device" refers to a device described in U.S. Pat. No. 6,287,521 by Quay et al. which is incorporated herein in its entirety. In one non-limiting example, a sample collection device for collecting a biological sample from a mammary organ of a patient may comprise a breast engaging member constructed of a non-porous material sized and dimensioned to receive at least a nipple portion of a breast of said patient and form a suction seal therewith; a solid phase sample collection medium in fluid connection with said breast engaging member for receiving a sample of expressed breast fluid; and a vacuum pump means in gaseous connection with said breast engaging member for generating negative pressure through the breast engaging member to facilitate breast fluid expression, wherein said solid phase sample collection medium is selected from the group consisting of microscopic glass slides, capillary tubes, collection tubes, columns, micro-columns, wells, plates, membranes, filters, resins, inorganic matrices, beads, particulate chromatographic media, plastic microparticles, latex particles, coated tubes, coated templates, coated beads, coated matrices, or a combination thereof. The sample collection device may include removable coupling means for removably coupling said sample collection housing with said breast engaging member. In some instances, the solid phase sample collection medium is supported by a support member integrally or removably mounted within said sample collection housing in fluid connection with said breast engaging member. The support member may be disc-shaped and is interposed between said breast engaging member and said sample collection housing. Further, the support member may have upper and lower retaining rings and supports a sheet of absorbent or adsorbent material. Support member supports may be a solid phase sample collection template including, but not limited to, capillary tubes, coated tubes, columns, micro-columns, plates, wells and microscopic slides, or a combination thereof. Support members define a fluid-retaining well and include at least one air channel to allow negative pressure to pass through the air channel to and from said breast engaging member. The solid phase sample collection medium may be a particulate medium contained within a cartridge removably mounted within said sample collection housing and having a first end of said cartridge in fluid connection with said breast engaging member where the first end of said cartridge is covered by a porous barrier material.

In another aspect, provided herein is a system for analyzing nipple aspirate fluid from an individual in need thereof comprising: an absorbent paper as illustrated in FIG. 1, the absorbent paper comprising microcellulose, mixed cellulose ester paper, or nitrocellulose; and a microscope for visualizing total protein of the nipples aspirate fluid, counting the number cells from the nipple aspirate fluid sample, or a combination thereof.

In another aspect, provided herein is a system for analyzing a nipple aspirate fluid (NAF) sample from an individual in need thereof comprising: an absorbent paper as illustrated in FIG. 1 for absorbing the nipple aspirate fluid sample, the absorbent paper comprising microcellulose, mixed cellulose ester paper, or nitrocellulose; and a microscope for visualizing total protein of the nipple aspirate fluid sample, counting the number cells of the nipple aspirate fluid sample, or a combination thereof.

In one embodiment, the total amount of protein in the nipple aspirate fluid is detected by staining said absorbent paper with a colloidal metal. For example, the colloidal metal may be colloidal gold or colloidal silver.

The system may, in some embodiments, further comprise an optionally networked computer processing device configured to perform executable instructions; and a computer program, the computer program comprising a software module executed by the computer processing device to apply a model or algorithm for analyzing the total protein content, the number of cells of the nipple aspirate fluid, or a combination thereof.

In one embodiment, the computer program may further comprise a software module executed by the computer processing device to designate a treatment regimen for the individual.

In another embodiment, or in addition, the computer program may further comprise a software module executed by the computer processing device to store photomicrograms in a database of photomicrograms.

In another embodiment, or in addition, the computer program may further comprise a software module executed by the computer processing device to store analysis in a database of analyses.

In another embodiment, or in addition, the computer program may further comprise a software module executed by the computer processing device to compare the total protein content or number of cells of the nipple aspirate fluid to a standard.

In another embodiment, or in addition, the computer program may further comprise a software module executed by the computer processing device to transmit an analysis to a health care provider or the individual.

In another embodiment, or in addition, the computer program may further comprise a software module executed by the computer processing device to transmit a diagnosis to a health care provider or the individual.

In another embodiment, or in addition, the computer program may further comprise a software module executed by the computer processing device to generate a report comprising the analysis.

In another aspect, provided herein is a non-transitory computer-readable storage media encoded with a computer program including instructions executable by a computer processing device to create an application, the application comprising a software module configured to apply a model or algorithm for analyzing the total protein content of a nipple aspirate fluid sample from an individual, the number of cells of a nipple aspirate fluid sample from an individual, or a combination thereof; and a software module configured to designate a treatment regimen for the individual.

In yet another aspect, provided herein is a non-transitory computer-readable storage media encoded with a computer program including instructions executable by a computer processing device to create an application, the application comprising: a software module configured to apply a model or algorithm for analyzing the total protein content and/or the number of cells of a nipple aspirate fluid sample absorbed onto an absorbent paper as illustrated in FIG. 1, and a software module configured to designate a treatment regimen for the individual.

In one embodiment, the model or algorithm comprises comparing the total protein content of the nipple aspirate fluid or the number of cells of the nipple aspirate fluid sample to a standard.

In yet another aspect, provided herein is a method of identifying women at low risk of future breast cancer comprising (a) obtaining a sample of nipple aspirate fluid on an absorbent paper as illustrated in FIG. 1, wherein said absorbent paper comprises microcellulose, mixed cellulose ester paper or nitrocellulose; (b) detecting the total amount of protein in said sample; (c) determining the number cells from said sample; and (d) identifying a woman as low lowest risk for breast cancer wherein the sample contains protein and is acellular.

In yet another aspect, provided herein is a method of identifying risk of a patient for breast cancer or diagnosing a patient at low risk of breast cancer comprising (a) collecting nipple aspirate fluid on an absorbent paper as illustrated in FIG. 1, wherein said absorbent paper comprises microcellulose, mixed cellulose ester paper or nitrocellulose; (b) washing said absorbent paper with a solution to collect cells, if any; (c) counting the number of cells in said sample and, optionally, determining the cytology of said cells, if any; (d) staining said absorbent paper with a metal particle suspension and determining the concentration of protein on said absorbent paper; (e) comparing, the concentration of protein in said nipple aspirate fluid and the number of cells in said fluid, to the concentration of protein and number of cells in a population of patients known to have breast cancer, to a population of patients known not to have breast cancer, or to a combination thereof; and (f) identifying a patient as at risk for breast cancer or at low risk of breast cancer wherein the sample contains protein and is acellular or contains one cell.

In yet another aspect, provided herein is a method of diagnosing risk of a patient for breast cancer comprising (a) collecting nipple aspirate fluid (NAF) on an absorbent paper as illustrated in FIG. 1, wherein said absorbent paper comprises microcellulose, mixed cellulose ester paper or nitrocellulose, wherein said NAF sample is obtained from classical providers and non-providers; (b) washing said absorbent paper with buffered solution to collect cells, if any; (c) counting the number of cells in said sample and, optionally, determining the cytology of said cells, if any; (d) staining said absorbent paper with colloidal gold or colloidal silver and determining the concentration of protein on said absorbent paper; (e) comparing, the concentration of protein in said nipple aspirate fluid and the number of cells in said fluid, to the concentration of protein and number of cells in a population of patients known to have breast cancer, to a population of patients known not to have breast cancer, or to a combination thereof; and (f) diagnosing a patient as at risk for breast cancer wherein the sample contains protein and is acellular or contains one cell. In yet another aspect, provided herein is a method of detecting protein in a sample of nipple aspirate fluid (NAF) comprising collecting the NAF on an absorbent paper as illustrated in FIG. 1, wherein said absorbent paper comprises microcellulose, mixed cellulose ester paper or nitrocellulose; and detecting the protein with a colloidal metal particle suspension, wherein the method can detect protein at a concentration of between 0.5 ng and 500 ng per sample.

In yet another aspect, provided herein is a test material for a risk associated with breast cancer comprising an absorbent paper as illustrated in FIG. 1, wherein said absorbent paper comprises microcellulose, mixed cellulose ester paper or nitrocellulose, a sample of nipple aspirate fluid collected from a women classically characterized as a non-yielder of nipple aspirate fluid, and a stain the detects the presence of protein from the nipple aspirate fluid collected on the absorbent paper.

Provided herein is an absorbent paper that is sized to cover a nipple, comprising microcellulose, mixed cellulose ester paper or nitrocellulose. The absorbent paper may comprise absorbent paper as illustrated in FIG. 1. In one embodiment, the absorbent paper comprises mixed cellulose ester paper. In another embodiment, the absorbent paper is from about 1.0 to about 3.0 inches in diameter and from about 0.01 to about 0.1 inches thick. In another embodiment, the absorbent paper comprises an L-shaped element 4 as illustrated in FIG. 1.

Provided herein is a composition comprising nipple aspirate fluid (NAF) and an absorbent paper that is sized to cover a nipple, comprising microcellulose, mixed cellulose ester paper or nitrocellulose.

Provided herein is a system for analyzing a nipple aspirate fluid (NAF) sample from an individual in need thereof comprising: an absorbent paper for absorbing the nipple aspirate fluid sample, the absorbent paper comprising microcellulose, mixed cellulose ester paper, or nitrocellulose, wherein the absorbent paper is sized to cover a nipple; and a breast pump device.

In one embodiment, the absorbent paper is from about 1.0 to about 3.0 inches in diameter and from about 0.01 to about 0.1 inches thick.

In another embodiment, the breast pump device is a MASCT™ device.

Disclosed herein, in certain embodiments, is a system for analyzing a nipple aspirate fluid (NAF) sample from an individual in need thereof comprising: (a) an absorbent paper for absorbing the nipple aspirate fluid sample, the absorbent paper comprising microcellulose, mixed cellulose ester paper, or nitrocellulose, wherein the absorbent paper is sized to cover a nipple; and (b) colloidal metal stain for determining the total protein of the nipple aspirate fluid sample. In some embodiments, the absorbent paper is from about 1.0 to about 3.0 inches in diameter and from about 0.01 to about 0.1 inches thick. In some embodiments, the system further comprises a microscope for visualizing total protein of the nipple aspirate fluid sample, counting the number cells of the nipple aspirate fluid sample, or a combination thereof. In some embodiments, the colloidal metal is colloidal gold or colloidal silver. In some embodiments, the system further comprises: an optionally networked computer processing device configured to perform executable instructions; and a computer program, the computer program comprising a software module executed by the computer processing device to apply a model or algorithm for analyzing the total protein content of the nipple aspirate fluid sample, the number of cells of the nipple aspirate fluid sample, or a combination thereof. In some embodiments, the computer program further comprises a software module executed by the computer processing device to designate a treatment regimen for the individual. In some embodiments, the computer program further comprises a software module executed by the computer processing device to store photomicrograms in a database of photomicrograms. In some embodiments, the computer program further comprises a software module executed by the computer processing device to store analysis in a database of analyses. In some embodiments, the computer program further comprises a software module executed by the computer processing device to compare the total protein content or number of cells of the nipple aspirate fluid sample to a standard. In some embodiments, the computer program further comprises a software module executed by the computer processing device to transmit an analysis to a health care provider or the individual. In some embodiments, the computer program further comprises a software module executed by the computer processing device to transmit a diagnosis to a health care provider or the individual. In some embodiments, the computer program further comprises a software module executed by the computer processing device to generate a report comprising the analysis. In some embodiments, said absorbent paper is a device as shown in FIG. 1.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the disclosure are set forth with particularity in the appended claims. A better understanding of the features and advantages of the present compositions, kits and methods will be obtained by reference to the following detailed description that sets forth illustrative embodiments, in which the principles of the disclosure embodiments are utilized, and the accompanying drawings of which:

FIGS. 1A-B illustrate a 2-D image of a representative absorbent paper or membrane described herein. Angular dimensions are provided in inches±1° and in degrees. FIG. 1A illustrates a top view of the paper or membrane. FIG. 1B illustrates a side angle production.

DETAILED DESCRIPTION OF THE INVENTION

Although there are currently several tests for breast cancer, more sensitive and reliable methods are needed to detect small, early stage, in situ carcinomas of the breast. Such methods should significantly improve breast cancer survival, as suggested by the successful employment of Papinicolou smears for early detection and treatment of cervical cancer.

The methods of the embodiments provided herein may be conducted with an appropriate breast pump device which may be used for sample collection such as, for example a device described in U.S. Pat. Nos. 5,798,266; 6,689,073; and 6,887,210, each of which is incorporated herein by reference. In one embodiment, the device is a MASCT™ device.

Methods and devices for obtaining, handling, and processing biological samples from mammary fluid are also described herein. Preferably, these methods are non-invasive, meaning they are non-surgical and do not involve penetration of the breast by needles or other intrusive devices. The devices and methods described herein are effective to collect mammary fluid alone or in conjunction with oxytocin stimulation.

Briefly, to practice noninvasive sample collection, the specialized breast pump devices feature a breast engaging portion or member coupled with a vacuum pump mechanism and may be fluidly connected with a solid phase sample collection medium.

The mammary fluid collection devices are typically provided as a specialized breast pump which can be applied to a human or animal breast covering the nipple and used in conjunction with a nipple touch procedure as described in more detail below following use of the device as described in Example 1.

The nipple touch procedure may be administered by applying a separate absorbent paper or membrane as described herein to each nipple.

Absorbent papers 2 (which may also be called "membranes" herein) which may be used in the disclosed methods and may be any material that is suitable to collect epithelial cells and biomarkers such as, for example, proteins, carbohydrates, lipids, nucleic acids, RNA, DNA, etc. Absorbent papers 2 include those made of, for example, nitrocellulose, microcellulose, mixed cellulose ester, or any other appropriate material for nipple fluid sample collection. While FIG. 1A illustrates a circular absorbent paper, other shapes such as, for example, ovals, squares, triangles, other polygons, are also contemplated herein so long as the shape accommodates sample collection.

In some embodiments, the absorbent paper 2 does not cause papers cuts to the nipple and/or the areola. In some embodiments, the absorbent paper 2 is shaped to avoid paper cuts to the nipple and/or areola.

The absorbent paper 2 is formed by stamping the paper out of large paper stock with a metal mold. The absorbent paper 2 is big enough to cover or partially cover the nipple. In some embodiments, the absorbent paper 2 is big enough to cover the nipple. Therefore, an absorbent paper may be from about 1.0 inches to about 3.0 inches in diameter or length at its average dimension A across any size of the absorbent paper. An absorbent paper 2 may be, for example, about 1.0, about 1.1, about 1.15, about 1.2, about 1.25, about 1.3, about 1.35, about 1.4, about 1.45, about 1.5, about 1.55, about 1.6, about 1.65, about 1.7, about 1.75, about 1.8, about 1.85, about 1.9, about 1.95, about 2.0, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, or about 3.0 inches in diameter. FIG. 1A provides a non-limiting example of an absorbent paper 2 that is 1.85 inches in diameter A. In some embodiments, the absorbent paper 2 covers or partially covers the areola of a breast. In some embodiments, the absorbent paper 2 covers the areola of a breast. In some embodiments, the absorbent paper 2 partially covers the areola of a breast. In some embodiments, the absorbent paper covers a nipple and does not extend to the areola of a breast.

The thickness of the absorbent paper 2 may vary to allow for optimal sample collection and includes materials that are from about 0.01 inches to about 0.1 inches in thickness. For example, the absorbent paper 2 may be about 0.01, about 0.02, about 0.03, about 0.04, about 0.05, about 0.06, about 0.07, about 0.08 about 0.09, or about 0.1 inches thick. FIG. 1B provides a non-limiting example of an absorbent paper 2 that is 0.05 inches thick. One would understand that, while FIG. 1B illustrates the side view of an absorbent paper 2 that is 0.05 inches thick, the thickness can be varied as well.

The L-shaped element (which may also be identified as a "slit" herein) is optional and is useful if the absorbent paper 2 is placed in a pressure modifying device to lower the pressure and cause egress of fluid from the inside of the breast. In one embodiment, the absorbent paper 2 is sized such that it fits into a modified breast pump, and the dimensions are set accordingly. Modified breast pumps that may be optionally used in connection with an absorbent paper 2 are described herein.

The L-shaped element 4 in FIG. 1A is a cut out that remains after the die cut has stamped the paper. In one non-limiting example, the L-shaped element is 0.063 E inches across when cut out in the stamping process. In an absorbent paper 2 that is 1.85 inches A in diameter or length at its average dimension across any size of the device, the ends of the L-shaped element 4 are 0.25 inches B from the mid-line of the absorbent paper 2. The angle D of the L-shaped element 4 can be any angle from 10 degrees to 170 degrees D. In one non-limiting embodiment, the angle D is 75 degrees as illustrated in FIG. 1A. The inner circle 6 illustrated in FIG. 1A is approximately 0.75 inches C in diameter and was designed such that the L-shaped flap 8 moves properly when used in a breast pump device (e.g., a MASCT™ device described herein). The dash symbols designating the inner circle 6 illustrate guide lines in the FIGURE. The slit 4 is shown by the incomplete triangle and is shaped as illustrated to form an incomplete circle. One would understand that the measurements described herein can be proportionally adjusted based upon the total size of the absorbent paper.

FIG. 1A represents the top view of one non-limiting example of an absorbent paper 2. The dash lines are not cut lines, but rather, are presented for ease of manufacturing to align the L-shaped element 4 such that the center of the absorbent paper 2 fits above the nipple area and so flap 8 sufficiently covers the nipple.

In another embodiment, the absorbent paper 2 is made of mixed cellulose ester and is formed in the shape and dimensions as illustrated in FIGS. 1A and 1B.

During or after administration of the breast pump device to produce mammary fluid, a biological sample is collected from the expressed mammary fluid using the absorbent paper, which sample may contain one or more of whole mammary fluid, whole cells, cell fragments, cell membranes, selected liquid, cellular or other solid fractions of the mammary fluid, as well as proteins, glycoproteins, peptides, nucleotides (including DNA, RNA, etc.) and other like biochemical and molecular constituents of the mammary fluid.

In certain embodiments of the invention, the expressed mammary fluid is contacted with a solid phase sample collection medium fluidly connected with the breast pump, simultaneous with or subsequent to the time of breast fluid expression. Suitable solid phase media in this context include microscopic glass slides, capillary tubes, coated tubes, microtiter wells or plates, membranes, filters, affinity columns, dot blot matrices, beads, resins, and other like media that will selectively adsorb, bind, filter, partition or otherwise process desired components of the mammary fluid for convenient incorporation into a desired assay.

Provided herein is a method of identifying women at low risk of future breast cancer, comprising obtaining a sample of nipple aspirate fluid; testing for protein in said sample; and testing for cells in said sample, wherein the lowest risk is associated with a sample that contains protein and is acellular.

Also provided herein is a method of identifying risk of a patient for breast cancer or diagnosing a patient at low risk of breast cancer, comprising: comparing, using a general purpose computer, the concentration of protein in a nipple aspirate fluid sample and the number of cells in said sample, to the concentration of protein and number of cells in a population of patients known to have breast cancer and/or to a population of patients known not to have breast cancer; wherein the lowest risk is associated with a sample that contains protein and is acellular or contains one cell.

The patient population identified as being at lowest risk for breast cancer is associated with a sample that contains protein and is acellular or contains one cell. In one embodiment, the sample contains no cells (i.e., is acellular). In another embodiment, low risk is associated with a sample that contains protein and contains one cell. The risk of breast cancer increases with increasing number of cells.

Patients to be diagnosed with a method provided herein include those classically designated as non-secretors and secretors of nipple aspirate fluid (NAF).

In one embodiment, the patient is classically designated as a non-secretor of nipple aspirate fluid.

Nipple aspirate fluid sample is collected on absorbent paper or membrane. Absorbent paper or membrane that may be used in the present methods includes paper of the size and dimensions as illustrated in FIG. 1. The absorbent paper or membrane may contain, for example, microcellulose, mixed cellulose ester or nitrocellulose. This new design results in significantly fewer cuts to nipple tissue during sample collection compared to paper that is currently marketed for NAF collection.

The absorbent paper or membrane is washed and the effluent is collected and assessed for number of cells. In one embodiment, cytology of cells, if any, in said sample is analyzed using any conventional method including, but not limited to, microscopy, flow cytometry, immunohistochemistry, or a combination thereof. A clinician can determine if cells, if present in the sample, are normal contain one or more characteristics of cancer cells. In one non-limiting example, cell samples may be stained with hemolysin and eosin.

Protein measured by the methods described herein is total protein content of the sample. The paper is then exposed to colloidal gold or colloidal silver and the total protein content (concentration) is determined using conventional methods or those described herein.

In one aspect, if a sample contains from about 50 pg to about 0.5 ng of protein, and does not contain cells, a patient is identified as being at low risk for breast cancer.

Alternatively, if the sample contains at least about 300 ng of protein and two (2) or more cells, a patient is identified for further evaluation of breast cancer or diagnosed as at medium or high risk for breast cancer. In one embodiment, the concentration of protein in a sample is from about 300 ng of protein to about 2 µg of protein and a patient is diagnosed at being at higher risk for breast cancer and, in some cases, is identified for further assessment. The cell fraction of the sample, in such a case, may contain about 2 cells to about 50 cells. Such a cell fraction may, in another case, may contain at least ten (10) cells.

Provided herein is an absorbent paper or membrane having the characteristics and dimensions as illustrated in FIG. 1, where the absorbent paper or membrane is made using microcellulose, mixed cellulose ester or nitrocellulose. In one embodiment, the absorbent paper or membrane comprises mixed cellulose ester.

A significant advance of the present absorbent paper or membrane is that is does not cut tissue to the extent that current filter paper does; thus, a patient undergoing assessment is subject to less pain and discomfort during the collection procedure. In one embodiment, tissue exposed to the absorbent paper or membrane is nipple tissue.

Provided herein is the use of the absorbent paper or membrane of as described herein in a method of identifying a patient at low risk of breast cancer or diagnosing a patient at low risk of breast cancer. In one aspect, the absorbent paper or membrane is used in any of the methods described herein or in any other method of nipple aspirate fluid collection for any use.

A method of detecting protein in a sample of nipple aspirate fluid (NAF) comprising collecting the NAF on an absorbent paper or membrane and detecting the protein with a colloidal metal particle suspension, wherein the method can detect protein at a concentration of between 0.5 ng and 500 ng per sample. The metal particle suspension may contain colloidal gold or colloidal silver. In one embodiment, the metal particle suspension comprises colloidal gold.

Provided herein is method of identifying risk of a patient for breast cancer or diagnosing a patient at low risk of breast cancer, comprising: collecting nipple aspirate fluid on absorbent paper or membrane; washing said absorbent paper or membrane with buffered solution to collect cells, if any; counting the number of cells in said sample and, optionally, determining the cytology of said cells, if any; staining said absorbent paper or membrane with colloidal gold or colloidal silver and determining the concentration of protein on said filter paper; and comparing, the concentration of protein in said nipple aspirate fluid and the number of cells in said fluid, to the concentration of protein and number of cells in a population of patients known to have breast cancer and/or to a population of patients known not to have breast cancer; wherein the lowest risk is associated with a sample that contains protein and is acellular or contains one cell.

Provided herein is a method of diagnosing risk of a patient for breast cancer, comprising: collecting nipple aspirate fluid on absorbent paper or membrane, wherein said NAF sample is obtained from classical providers and non-providers; washing said absorbent paper or membrane with buffered solution to collect cells, if any; counting the number of cells in said sample and, optionally, determining the cytology of said cells, if any; staining said absorbent paper or membrane with colloidal gold or colloidal silver and determining the concentration of protein on said filter paper; and comparing, the concentration of protein in said nipple aspirate fluid and the number of cells in said fluid, to the concentration of protein and number of cells in a population of patients known to have breast cancer and/or to a population of patients known not to have breast cancer; wherein the lowest risk is associated with a sample that contains protein and is acellular or contains one cell.

In one embodiment, the sample is acellular and the patient is identified as at the lowest risk for breast cancer. In another embodiment, the sample contains one cell and the patient is identified as at low risk for breast cancer. In yet another embodiment, the sample contains more than 2 cells and the patient is identified for further assessment.

In one embodiment, the total protein concentration of each breast is determined and, if the total protein concentration of one sample is greater than 300 ng, the patient is identified for further assessment of breast cancer. Alternatively, the total protein concentration of each breast is determined and, if the total protein concentration of each sample is at, or below 200 ng protein, the patient is identified as being at low risk for breast cancer.

In one embodiment, the nipple aspirate fluid is collected on an absorbent paper or membrane following massaging of breast tissue and suction with a MASCT™ device as described in Example 1 below. As used herein, a "MASCT™ device" refers to a device described in U.S. Pat. No. 6,287,521 by Quay et al. which is incorporated herein in its entirety. In one non-limiting example, a sample collection device for collecting a biological sample from a mammary organ of a patient may comprise a breast engaging member constructed of a non-porous material sized and dimensioned to receive at least a nipple portion of a breast of said patient and form a suction seal therewith; a solid phase sample collection medium in fluid connection with said breast engaging member for receiving a sample of expressed breast fluid; and a vacuum pump means in gaseous connection with said breast engaging member for generating negative pressure through the breast engaging member to facilitate breast fluid expression, wherein said solid phase sample collection medium is selected from the group consisting of microscopic glass slides, capillary tubes, collection tubes, columns, micro-columns, wells, plates, membranes, filters, resins, inorganic matrices, beads, particulate chromatographic media, plastic microparticles, latex particles, coated tubes, coated templates, coated beads, coated matrices, or a combination thereof. The sample collection device may include removable coupling means for removably coupling said sample collection housing with said breast engaging member. In some instances, the solid phase sample collection medium is supported by a support member integrally or removably mounted within said sample collection housing in fluid connection with said breast engaging member. The support member may be disc-shaped and is interposed between said breast engaging member and said sample collection housing. Further, the support member may have upper and lower retaining rings and supports a sheet of absorbent or adsorbent material. Support member supports may be a solid phase sample collection template including, but not limited to, capillary tubes, coated tubes, columns, micro-columns, plates, wells and microscopic slides, or a combination thereof. Support members define a fluid-retaining well and include at least one air channel to allow negative pressure to pass through the air channel to and from said breast engaging member. The solid phase sample collection medium may be a particulate medium contained within a cartridge removably mounted within said sample collection housing and having a first end of said cartridge in fluid connection with said breast engaging member where the first end of said cartridge is covered by a porous barrier material.

Prior to, or concurrent with, each assay run of the invention, it may be useful to perform a preliminary evaluation to verify sample origin and/or quality if sufficient sample quantity can be obtained. The focus of such preliminary evaluations is to verify that the sample collected from expressed mammary fluid is indeed of mammary origin, and is not contaminated with other potential contaminants, such as sweat from skin surrounding the nipple. For these sample verification purposes, a variety of assays are available which identify mammary fluid markers known to be present in mammalian mammary fluid, and which are preferably highly specific markers for mammary fluid (i.e. markers which are typically always present in mammary fluid and which are absent from all, or most of, other potentially contaminating bodily fluids and tissues). However, an acceptable level of specificity for mammary fluid markers within the methods of the invention is provided by markers that are simply known to be present in mammary fluid, even though they may be present in other bodily fluids. One such marker is the enzyme lysozyme, which is a normal component of human serum, urine, saliva, tears, nasal secretions, vaginal secretions, seminal fluid, and mammary fluid. Lysozyme (muramidase) is an enzyme which hydrolyzes beta 1,4-glycosidic linkages in the mucopolysaccharide cell wall of a variety of microorganisms resulting in cell lysis. Quantitative measurement of lysozyme is readily accomplished by a well known agar plate diffusion method, described in detail in the instructions provided with the Quantiplate® lysozyme test kit, available from Kallestad, Sanofi Diagnostics (Chasta, Minn.), incorporated herein by reference in its entirety.

Other mammary fluid markers for sample verification that are more specific than lysozyme are preferred within the methods of the invention, and can be readily incorporated within the method embodiments based on published and generally known information. Useful among these markers are proteins and other biological substances that are specifically expressed or enriched in mammary fluid. A diverse array of suitable markers in this context have been characterized and have already been used to develop specific antibodies, including affinity purified and monoclonal antibodies. These antibodies can in turn be employed as immunological probes to determine the presence or absence, and/or to quantify, selected mammary fluid markers to verify mammary fluid sample origin and quality. Mammary fluid markers of particular interest for use within the invention include specific cytokeratins that are characteristically expressed by normal and cancerous mammary epithelial cells, against which specific panels of antibody probes have already been developed. (See for example, Nagle, J., Histochem. Cytochem. 34:869-881, 1986, incorporated herein by reference in its entirety). Also useful as mammary fluid markers are the human mammary epithelial antigens (HME-Ags) corresponding to glycoprotein components of the human milk fat globulin (HMFG) protein, against which specific antibodies (e.g., anti HMFG1, Unipath, U.K.) are also available. (See Rosner et al., Cancer Invest. 13:573-582, 1995; Ceriani et al. Proc. Natl. Acad. Sci. USA 74:582-586, 1982; Ceriani et al., Breast Cancer Res. Treat. 15:161-174, 1990, each incorporated herein by reference in its entirety).

The term "colloidal metal particles" used in this connection is meant to include dispersions of particles, preferably sols, consisting of a metal, a metal compound or nuclei coated with a metal or metal compound. Colloidal metal particles can be prepared following art-known procedures, such as have been described for preparing suspensions of gold, silver, platinum or iron hydroxide and the like. The terms "gold colloid" and "colloidal gold composition" used herein refer to a suspension of sub-micrometer-sized gold particles evenly dispersed in a fluid (e.g., water or an aqueous buffer). The colloidal gold composition utilized in the quantification assay contains highly concentrated gold particles. In one example, the colloidal gold composition has a gold particle concentration ranging from $3.5 \times 10^{12}$ to $7.0 \times 10^{12}$ particles/ml, e.g., $(3.5-5.25) \times 10^{12}$ particles/ml.

The present methods may be performed using conventional techniques of immunocytochemistry such as for example immunogold labeling. Such procedures are described, for example, in the following texts that are incorporated by reference: (1) Colloidal Gold-Principles, Methods and Applications, Hayat M, (1989-1990) (3 volumes), Academic Press. (Hardback); (2) Colloidal Gold-A New Perspective For Cytochemical Marking, Beesley J (1989), Royal Microscopical Society Handbook No 17. Oxford Science Publications. Oxford University Press. (Paperback); (3) An Introduction To Immunocytochemistry: Current techniques and problems, Polak J and Van Noorden 5 (1984) Royal Microscopical Society Handbook No 11. Oxford Science Publications. Oxford University Press. (Paperback); (4) Immunocytochemistry-Modern Methods and Applications, Polak J and Van Noorden 5 (1986) (2nd ed.), Butterworth Heinemann, Oxford. (Hardback); and (5) Techniques in Immunocytochemistry, Bullock G and Petmsz P (1982-1989) (4 volumes) Academic Press.

Procedures are also described, for example, in Marc Moermans, et al., "Sensitive Colloidal Metal (Gold or Silver) Staining of Protein Blots on Nitrocellulose Membranes" in Analytical Biochemistry 145, 315-321 (1985); Danscher et al., Colloidal Gold Amplification, the Journal of Histochemistry and Cytochemistry, 31: No. 12, 1394-1398 (1983); De Mey, Colloidal Gold Methods, Immunocytochemistry, Chapt. 6, pp. 82-112 (1983); and U.S. Pat. No. 4,920,059 by Moermans et al.

Examples of colloidal metal particles that will bind to proteins and nucleic acids when adjusted to the optimal pH and concentration are the metals platinum, gold, silver and copper, and the metal compounds for example, gold, silver, platinum, iron, or copper compounds, such as, silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulfide, manganese hydroxide, lead sulfide, mercury sulfide, barium sulfate and titanium dioxide. Colloids consisting of nuclei, coated with the above mentioned metals or metal compounds can also be used. The particles have similar properties as the metal or metal compound colloids, but size, density and metal content can be optimally combined. In general, all colloidal metal particles or metal compounds which can be adjusted to the optimal pH for protein binding and which give a color intensity in protein staining, sufficient to be observed by the naked eye, can be used. Preferably, the sensitivities are equal or superior to those obtained with the metals gold and silver.

For the staining of proteins, particularly good results are obtained with gold, silver and iron hydroxide colloids.

The particle size of the colloidal metal or metal compound particles may be between about 1 and about 100 nm. The appropriate pH is the pH at which binding is maximal and the most intense color is obtained. Maximal binding may occur when the proteins and the colloidal metal particles have opposite net charges. In this process, the proteins interact with colloidal metal particles at a pH close to the pI of the protein. Adjustment of the pH can be achieved in any of the usual ways. Addition of a stock buffer to about a 10 mM final concentration to the colloidal metal particles represents one method for use herein.

The appropriate concentration of the colloidal metal particles is one that gives full color saturation within practical incubation times (from a few minutes to one day). It can be obtained by choosing the proper concentrations of the raw materials with which they are prepared, or by dilution or concentration by art-known methods.

In some instances, the absorbent paper or membrane is washed prior to the staining procedure. This washing may be used remove adherent interfering materials. Such washing of the absorbent paper or membrane may be done by contacting it with a buffer solution or water optionally supplemented with at least one substance which promotes the staining specificity defined as specific binding of the colloidal or metal compound particles to the proteins and the absence of such specific binding on those parts of the immobilizing matrix where no protein are immobilized. A detergent may be added as needed to the colloidal metal particles, before or after adjusting the pH. Such detergents are herein exemplified by Tween 20 (polyoxyethylene sorbitan monolaurate, Tween 80 (polyoxyethylene sorbitan mono-oleate), Triton X-100 (octyl phenoxy polyepoxy ethanol) and myristyltrimethyl ammonium bromide. It will be understood that similar detergents, i.e., surface active substances, may also be used. The detergent added to the colloidal metal particles may also be employed to promote the specific binding of the colloidal metal particles to the protein.

Optionally, the optical signal formed by the colloidal metal particles may be enhanced by appropriate enhancers such as physical developers, for example, silver- or gold-containing compounds or modified and/or enhanced by art-known color identification methods of metal ions after transformation of the colloidal metal into a metal ion.

Protein can be detected and quantitated using conventional means in the art such as, for example, reading the colored signal produced by and characteristic for the bound colloidal metal particles with the naked eye or using art-known spectrophotometric techniques such as densitometry. In such procedures, the optical density of the mixture can be measured at a wavelength ranging from 540-700 nm, and the concentration of the biomolecule is determined based on the value of the optical density. In one embodiment, the optical density is measured at 590 nm. Protein can be detected using the presently disclosed methods ad a concentration of, for example, about 0.5 pg, about 1 pg, about 100 pg, about 250 pg, about 350 pg, about 500 pg, about 750 pg, about 1 ng, about 100 ng, about 250 ng, about 500 ng, about 750 ng and about 1 µg. In one embodiment, protein is detected at about 0.5 ng.

Methods for washing cells from a matrix such as, for example, absorbent paper or membrane using a buffered solution are known in the art and contemplated herein. The effluent of such washings may be further analyzed using methods including, but not limited to, microscopy, immunocytochemistry and flow cytometry. For example, after washing the absorbent paper or membrane containing the nipple aspirate fluid sample to remove any cells, the wash solution may be assessed using microscopy and the number of cells in the solution is determined. The morphology of any cells present in the solution may be determined. Additionally, cells, if present, may be stained for one or more extracellular and/or intracellular markers to determine if the cells have a normal profile or have one or more markers indicative of cancer cells. For example, cells may be analyzed for the presence or absence of BRCA1, BRCA2, p63, a cyclin, a cytokeratin, or any other marker that may indicate that the cells are cancer cells or normal cells based on the presence, absence, or level of such markers. Labeled antibodies may also be used to stain cells in such samples using conventional flow cytometry techniques known in the art. Further methods of analyzing cells are provided herein below in Example 2.

Digital Processing Device

In some embodiments, the methods, systems, and software described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

Non-Transitory Computer Readable Storage Medium

In some embodiments, the methods, systems, and software disclosed herein include one or more computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the methods, systems, and software disclosed herein include at least one computer program, or use of the same. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The methods, systems, and software disclosed herein include, in various embodiments, software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the methods, systems, and software disclosed herein include one or more databases, or use of the same. In view of the disclosure provided herein, those of skill in the art will recognize that many databases are suitable for storage and retrieval of metagenomic information (including metagenomic profiles), metatranscriptome information (including metatranscriptome profiles), and multiplex profiles. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local storage devices.

In order that those skilled in the art may be better able to practice the compositions and methods described herein, the following example is given for illustration purposes.

EXAMPLES

Example 1

Assessment of Nipple Aspirate Fluid

This trial was a single-center study involving three (3) healthy, non-pregnant, non-lactating female subjects. Subjects were enrolled in the order of appearance at the clinic.

The primary trial objective was to determine the percentage of women from age 30 to 65 that produces ductal fluid, as determined by the presence of protein on the nitrocellulose filter when using the MASCT™ device.

A secondary objective was to evaluate the nipple aspirate fluid cytologically for the presence and type of cells (if any).

Abbreviations

Abbreviations used herein include, for example, MAF: Mammary Aspiration Fluid; MASCT™: Mammary Aspiration Specimen Cytology Test; NA: Not Available; ND: Not Done; NR: Not Recorded; and NAF: Nipple Aspirate Fluid.

Methodology:

Briefly, a tared nitrocellulose filter was used to collect ductal fluid by just touching it to each nipple (one for each breast). Next, mammary fluid samples were aspirated using the MASCT™ device with a tared sample collection unit. Both sets of nitrocellulose filters were tested for protein using a staining technique described below. Cells collected from washing the filters containing nipple aspirate fluid specimens underwent cytological examination.

Assessment:

The primary endpoint of the trial was the percentage of women completing the trial that produce ductal fluid, as determined by the presence of protein on the nitrocellulose filter when using the MASCT™ device.

The secondary endpoint was the presence of cells in the nipple aspirate fluid as determined by cytologic evaluation.

Results:

With regard to the protein testing done of the filters obtained from these 3 subjects, none on the nipple wash filter samples showed the presence of protein. All filters from the MASCT™ device showed that protein was detected on the device filter.

Overall Study Design and Plan

The MASCT™ device had been previously cleared for marketing via the 510(k) regulatory pathway. This clinical study was designed to test modifications to the MASCT™ device that were made to enhance efficacy and usability and the ability to detect protein in nipple aspirate fluid from women, including those previously thought to be non-secreters. The clinical utility of nipple aspirate fluid for helping in breast health management has been hampered over the last 50 years by the current methodology of collecting and measuring the presence of fluid. In fact, with current technology up to 50% of all women are non-secretors, that is, they are judged to not produce NAF.

This was a single-center study involving the enrollment of up to 50 healthy non-pregnant, non-lactating female subjects. Subjects were enrolled in the order of appearance at the clinic.

Prior to entering the study, the investigator or designated assistant explained to each subject, the nature of the study, its purpose, procedures, expected duration, available alternatives, and the benefits and risks involved in study participation. Each subject was given a consent document and had the opportunity to ask questions; and was informed of her right to withdraw from the study at any time without prejudice. After this explanation, and before any study-specific procedures are performed, the subject voluntarily signed and dated an informed consent statement. Prior to participation in the study, each subject received a copy of the signed and dated written informed consent form and any other written information.

Inclusion/Exclusion Criteria Review and Pregnancy Evaluation

When necessary, each patient underwent a urine pregnancy test prior to further participation in the study. A positive pregnancy test would exclude the subject from participation. All inclusion and exclusion criteria were reviewed to ensure subject eligibility. After eligibility was established, a unique subject identification number was assigned.

Demographics and Medical History

The following demographic and medical history was obtained from each subject: age and ethnic origin; family medical history, especially mother and sisters; personal medical history, including breast cancer, benign breast conditions, and reproductive diseases (for example, ovarian or endometrial tumors); concomitant medications; age of menarche; age at first pregnancy; age at first live birth; age of menopause; and height and weight.

Breast Preparation

Subjects were placed in a recumbent position. The nipple and peri-aureolar areas of both breasts were cleansed with alcohol to remove excess skin oils, cosmetics or epithelial debris. After the alcohol evaporated, a warm moist compress was placed on both breasts for 10 to 15 minutes. The compresses were removed and the subjects were placed in a seated position. Alcohol was used to wipe the nipple area to remove any ductal plugs that were present.

Nipple Touch Procedure

All persons handling filter materials shall wear gloves and a protective mask to minimize the risk of filter contamination.

Device Cleaning Procedure

Prior to each subject use, the MASCT™ device was thoroughly cleaned with an antimicrobial solution such as CIDEX®. The device was not exposed to extreme temperatures or autoclaved. The device was inspected periodically for deterioration of the materials of the device or failure to induce negative pressure. If either condition was observed, the unit was replaced.

MASCT™ and Nipple Touch Procedures a. Label one filter disk assembly 'left' and a second filter disk assembly 'right'.

b. Weigh and record the weights of each assembly taking care to not touch the filter with a bare hand, and using forceps as needed.

c. Insert one assembly into the breast pump device.

d. Instruct the subject to perform manual self-breast massage beginning with the chest wall and moving gradually to the nipple-aureolar complex for approximately one minute.

e. The subject will then compress her breast with both hands while the breast pump device is actuated for 60-90 seconds by the physician or nurse practitioner.

f. Remove the filter disk assembly and weigh the MASCT™ filter disks for fluid collection.

g. Using an antimicrobial solution such as CIDEX®, wipe the surfaces of the sample collection funnel and rinse out the collection vial.

h. Repeat steps c, d, e, f and g for the second breast.

i. Store the filter disks in a refrigerator for subsequent evaluation of protein and/or cytology evaluation. The packaging for each filter disk assembly shall be appropriately labeled with subject ID number and date of collection.

Variations to this collection procedure may be conducted, but at no time will the number of massage/collection procedures exceed that allowed in the approved labeling for the MASCT™ device.

Subject Observation

Subjects will remain in the clinic and be observed for adverse device effects for 30 minutes following aspiration. If there are no evolving or unresolved adverse effects at that time, the subjects will be released. At the investigator's discretion, subjects experiencing any adverse effects at the end of this observation period will remain at the study site until either the effect resolves or follow-up arrangements have been made.

Conduct of the Study

All subjects in this study were studied according to the protocol described herein.

Three (3) subjects were enrolled and the disposition of patients is provided in the table below.

| SUBJECT DISPOSITION BY SUBJECT | | |
|---|---|---|
| Subject number | Enrolled | Completed Study |
| B01 | Yes | Yes |
| B02 | Yes | Yes |
| B03 | Yes | Yes |

The following table contains individual patient data listings for demographics. There were no deaths or serious adverse events.

| SUBJECT DEMOGRAPHICS | | | |
|---|---|---|---|
| | | | Active |
| Age | Mean | | 50 |
| | Std. Dev. | | 11.79 |
| | Median | | 53 |
| | Range | | 37-60 |
| Weight (kg) | Mean | | 135.5 |
| | Std. Dev. | | 20.5 |
| | Median | | 135.5 |
| | Range | | 115-156 |
| Height (cm) | Mean | | 64.5 |
| | Std. Dev. | | 3.04 |
| | Median | | 66 |
| | Range | | 61-66.5 |
| BMI | Mean | | 23.03 |
| | Std. Dev. | | 4.1 |
| | Median | | 25.2 |
| | Range | | 18.3-25.6 |
| | | N | % |
| Gender | Female | 3 | 100 |
| Ethnicity | Caucasian | 3 | 100 |

Discussion and Overall Conclusions

The following results were obtained upon testing of the individual filters used in this study.

Nipple Wash Results

None of the control nipple wash filter samples demonstrated any presence of protein.

Breast Pump Results

| Subject | Breast | Concentration of protein |
|---|---|---|
| Subject # 1 | Left Breast | 30 ng of protein |
| Subject # 1 | Right Breast | 868 pg of protein |
| Subject # 2 | Left Breast | 580 pg of protein |
| Subject #2 | Right Breast | 71 pg of protein |
| Subject # 3 | Left Breast | 7.1 ng of protein |
| Subject # 3 | Right Breast | 17.6 ng of protein |

Based on these results, it was determined that the MASCT™ device obtained nipple aspirate fluid as evidenced by the presence of protein.

Deaths or Serious Adverse Events

There were no deaths or serious adverse events.

Subsequent Data

In a study of 31 women aged 18-65, the method of this disclosure was used to analyze for protein and it was detected in all 31 women (one woman had protein detected in only one breast) giving a clinical utility of 97%. This improvement over the prior art makes this test useful for identifying women with early, precancerous changes when cancer prevention measures can be instituted.

A Summary of the Efficacy Evaluation

The primary objective of the study was achieved as determined by the presence of protein on all nitrocellulose filters obtained when using the MASCT™ device. The secondary objective of evaluating nipple aspirated fluid cytologically for the presence and type of cells was accomplished. All samples were successfully analyzed for cellular material.

Example 2

Cytology in Biological Samples From Mammary Fluid

This example describes the use of conventional cytological techniques to identify and assess cells obtained from samples described in Example 1. Following collection of the sample on the filter paper, the filter is washed using any suitable buffered wash solution (e.g., phosphate buffered saline) to collect cells, the fluid may be further processed and cells may be collected by, for example, centrifugation in a modified cytology vial. Processed samples are then transferred to the central region of a clean glass microscopic slide, and a cover slip is slid over the sample to spread it along the surface of the slide. The slide is allowed to air dry and then is fixed, for example in absolute alcohol, and stained with standard cytological stains, such as methylene blue, hematoxyln and eosin, or other suitable stain.

The slides are then examined by light microscopy for evidence of atypical growth of cells and clumps of cells, using well known methods, including those described in Diagnosis of Non-Palpable Breast Lesions: Ultrasonographically Controlled Fine-Needle Aspiration: Diagnostic and Prognostic Implications of Cytology by Jacqueline Mouriquand, S. Karger Pub., July 1993; Breast: Guides to Clinical Aspiration Biopsy by Tilde S. and Irwin K. Kline, Igaku-Shoin Medical Pub., May 1988; Cytopathology of the Breast (Asop Theory and Practice of Cytopathology by Shahla Masood, American Society of Clinical Pathology, November 1995; Fine Needle Aspiration Cytology and Its Clinical Applications: Breast and Lung by Philip S. Feldman, American Society of Clinical Pathology, November 1984; each incorporated herein by reference in its entirety.

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of identifying a risk of developing breast cancer in an individual in need thereof, the method comprising:
   a) detecting a total amount of protein and/or a number of cells in a nipple aspirate fluid sample absorbed onto a nipple covering comprising an absorbent paper, wherein said absorbent paper comprises microcellulose, mixed cellulose ester paper or nitrocellulose, and the absorbent paper having a diameter from about 1.0 inches to about 3.0 inches and a thickness from about 0.01 inches to about 0.1 inches, wherein the absorbent paper is sized to cover a nipple; and b) identifying the risk for developing breast cancer based on the total amount of protein and/or the number of cells of the nipple aspirate fluid sample.

2. The method of claim 1, wherein said absorbent paper is a device as illustrated in FIG. 1.

3. The method of claim 1, wherein said individual is identified as being at low risk for developing breast cancer where said nipple aspirate fluid sample contains protein and is acellular.

4. The method of claim 1, wherein said individual is identified as being at low risk for breast cancer where said nipple aspirate fluid sample contains from about 1 pg to about 500 ng of protein and is acellular.

5. The method of claim 1, wherein said individual is identified for further evaluation of breast cancer or diagnosed as at medium or high risk for breast cancer if said nipple aspirate fluid sample contains at least about 300 ng of protein and two or more cells.

6. The method of claim 1, wherein said individual is identified for further evaluation of breast cancer or diagnosed as at medium or high risk for breast cancer if said nipple aspirate fluid sample contains between about 300 ng of protein to about 2 µg of protein and two or more cells.

7. The method of claim 1, wherein said individual is identified for further evaluation of breast cancer or diagnosed as at medium or high risk for breast cancer if said nipple aspirate fluid sample contains between about 300 ng of protein to about 2 µg of protein, and between two and fifty cells.

8. The method of claim 1, wherein said individual is a diagnosed as a classical non-secretor or a classical secretor of nipple aspirate fluid.

9. The method of claim 1, wherein detecting the cells in the nipple aspirate fluid sample comprises washing the absorbent paper, collecting an effluent, and counting the cells in the effluent.

10. The method of claim 9, wherein the absorbent paper is washed before the total amount of protein is determined.

11. The method of claim 1, wherein the total amount of protein is detected by staining said absorbent paper with a metal particle suspension.

12. The method of claim 11, wherein the metal particle suspension is colloidal gold or colloidal silver.

13. The method of claim 1, wherein said number of cells is detected using a microscope.

14. The method of claim 1, further comprising collecting said nipple aspirate fluid sample on the absorbent paper following massaging of breast tissue, applying a suction, and retrieving said nipple aspiration fluid sample with a sample collection device configured for collecting a biological sample from a mammary organ of a patient.

* * * * *